US00PP27747P2

(12) United States Plant Patent
Miller

(10) Patent No.: US PP27,747 P2
(45) Date of Patent: Mar. 7, 2017

(54) ***PUNICA GRANATUM* PLANT NAMED 'PQ2009'**

(50) Latin Name: *Punica granatum*
Varietal Denomination: PQ2009

(71) Applicant: Michael A. Miller, Atlanta, GA (US)

(72) Inventor: Michael A. Miller, Atlanta, GA (US)

(73) Assignee: ITSAUL PLANTS LLC, Alpharetta, GA (US)

( * ) Notice: Subject to any disclaimer, the term of this patent is extended or adjusted under 35 U.S.C. 154(b) by 70 days.

(21) Appl. No.: 14/545,216

(22) Filed: Apr. 8, 2015

(51) Int. Cl.
*A01H 5/02* (2006.01)

(52) U.S. Cl.
USPC ..... Plt./210

(58) Field of Classification Search
USPC ..... Plt./210
See application file for complete search history.

*Primary Examiner* — Anne Grunberg
(74) *Attorney, Agent, or Firm* — Penny J. Aguirre

(57) ABSTRACT

A new cultivar of pomegranate tree, 'PQ2009', that is characterized by its flowers that consistently have 6 petals and 6 sepals that are bright orange in color and bloom from spring until first frost in Georgia, its flowers that are borne primarily at the terminals on soft to semi-hard wood, its foliage that is initially bronze in color maturing to a medium green color and persists until freeze (survives frosts), its production of quality tasting fruit on one year-old container grown plants that ripen in late summer to late fall, and its fruit that is sweet with low astringency and little aftertaste.

2 Drawing Sheets

Botanical classification: *Punica granatum.*
Varietal denomination: 'PQ2009'.

BACKGROUND OF THE INVENTION

The present invention relates to a new and distinct cultivar of pomegranate tree, botanically known as *Punica granatum* and hereinafter referred by its cultivar name, 'PQ2009'. 'PQ2009' is a new cultivar of pomegranate tree that blooms from spring to fall, produces sweet tasting fruit, and is both ornamental and productive as a large container or landscape plant.

'PQ2009' was selected by the Inventor as a seedling that arose from seed sown in 2009 from fruit of *Punica granatum* grown by a home gardener (cultivar name if any and patent status is unknown) that had been open pollinated (the male parent is unknown). The fruit of the female parent plant exhibited yellow skin, bright red arils, and a taste that was sweet, low in acidity and low in astringency and the goal was to obtain a new cultivar of *Punica granatum* that combined those desirable fruit characteristics with a floriferous blooming habit and good fruit production. 'PQ2009' was selected as a single unique plant in 2012 from among 100 seedlings that were evaluated.

Asexual propagation of the new cultivar was first accomplished by stem cuttings under the direction of the Inventor in Alpharetta, Ga. in February of 2011. Asexual propagation by stem cuttings has determined that the characteristics of this cultivar are stable and are reproduced true to type in successive generations.

SUMMARY OF THE INVENTION

The following traits have been repeatedly observed and represent the characteristics of the new pomegranate tree. These attributes in combination distinguish 'PQ2009' as a unique cultivar of pomegranate tree.

1. 'PQ2009' exhibits flowers that consistently have 6 petals and 6 sepals that are bright orange in color and bloom from spring until first frost in Georgia.
2. 'PQ2009' exhibits flowers that are borne primarily at the terminals on soft to semi-hard wood.
3. 'PQ2009' exhibits foliage that is initially bronze in color maturing to a medium green color and persists until freeze (survives frosts).
4. 'PQ2009' exhibits production of quality tasting fruit on one year-old container grown plants.
5. 'PQ2009' exhibits fruit that ripens in late summer to late fall with late production persisting on the tree through winter for ornamental value.
6. 'PQ2009' exhibits fruit that is sweet with low astringency and little aftertaste.

The fruit of the female parent plant of 'PQ2009' differs from 'PQ2009' in having yellow fruit that does not turn red at ripening. 'PQ2009' can be compared to *Punica granatum* cultivars 'Wonderful' (not patented), 'Granada' (not patented), 'Kamel' (U.S. Plant Pat. No. 21,966), and 'EMEK' (U.S. Plant Pat. No. 21,907). 'Wonderful' is similar to 'PQ2009' in having edible, medium soft seeds. 'Wonderful' differs from 'PQ2009' in having fruit that can get larger in size, in having fruit with darker red colored skin and arils, in having fruit with a more astringent, wine-like flavor, and in having foliage that is thicker and glossier. 'Granada' is similar to 'PQ2009' in having fruit that is low in acidity. 'Granada' differs from 'PQ2009' in having fruit with skin that is darker red and turns red before ripening, in having foliage that is thicker and glossier, and in having flowers that are red in color. 'Kamel' differs from 'PQ22009' in having fruit with darker red colored skin, in having flowers that are redder in color, and in having flowers with a variable numbers of 5-7 petals. 'EMEK' differs from 'PQ2009' having fruit that ripens earlier, in having flowers with a variable number of 5-7 petals, and in having flowers that are deep orange-red in color.

BRIEF DESCRIPTION OF THE DRAWINGS

The accompanying colored photographs illustrate the overall appearance and distinct characteristics of the new pomegranate tree, 'PQ2009'. The photographs were taken of two year-old plants as grown in 15-gallon containers in Alpharetta, Ga.

The photograph in FIG. 1 provides a view of the overall plant habit of 'PQ2009'.

Figure 1:
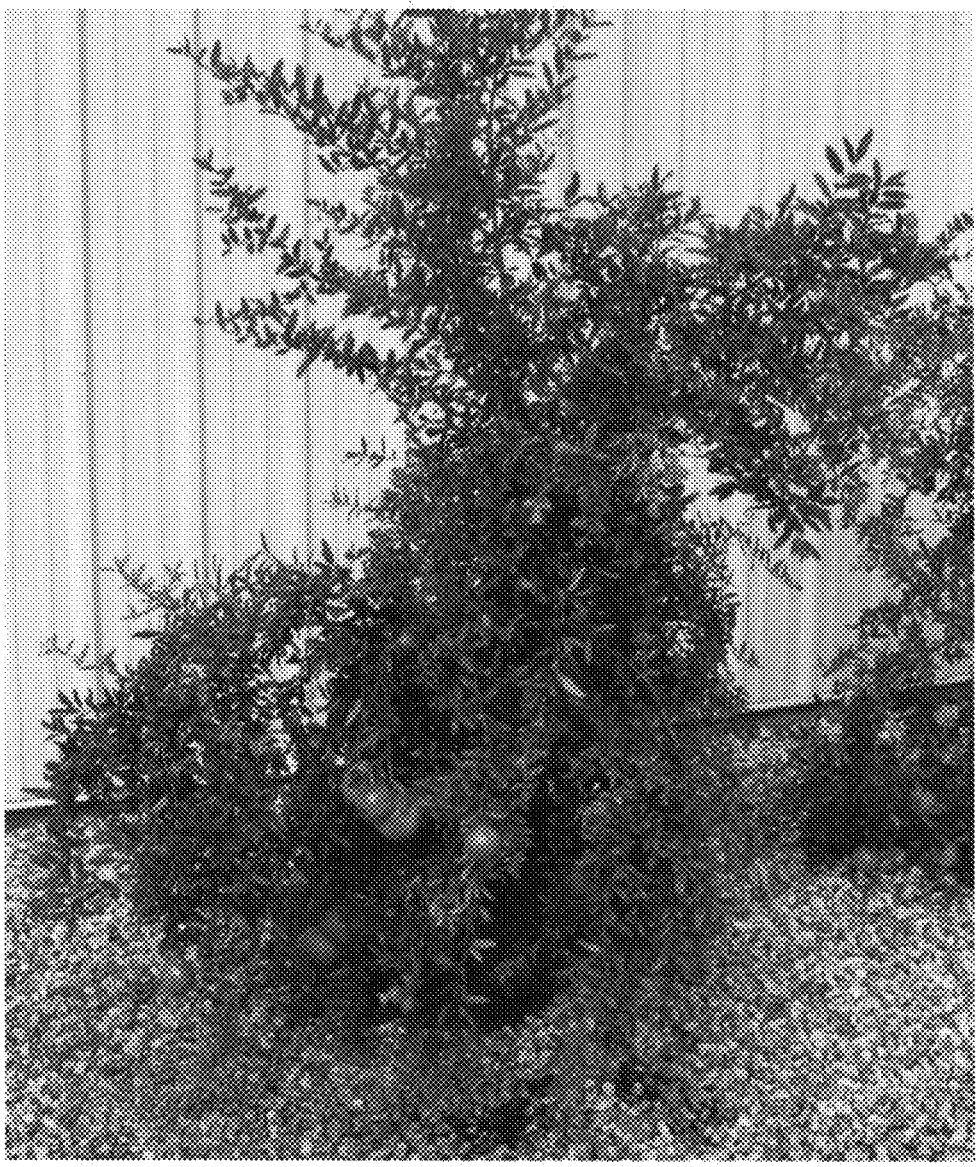
Figure 2:
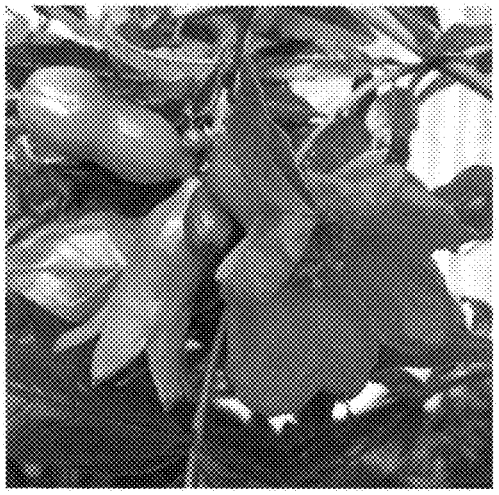

The photograph in FIG. 2 provides a close-up view of a mature flower of 'PQ2009'.

Figure 3:
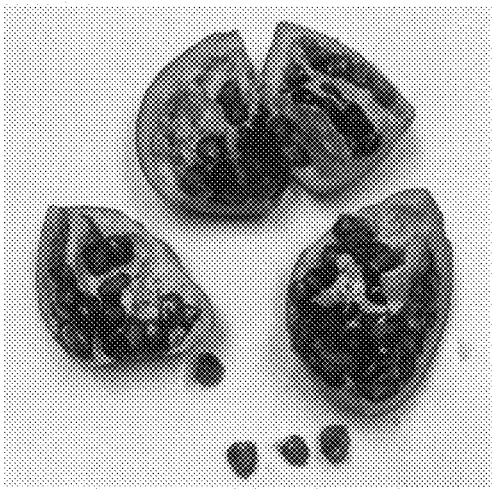

The photograph in FIG. 3 provides a view of the arils inside the mature fruit of 'PQ2009'.

Figure 4:
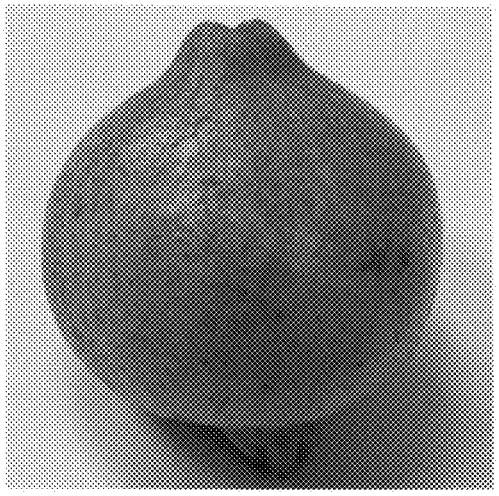

The photograph in FIG. 4 provides a close up view of a ripening fruit of 'PQ2009'.

Figure 5:
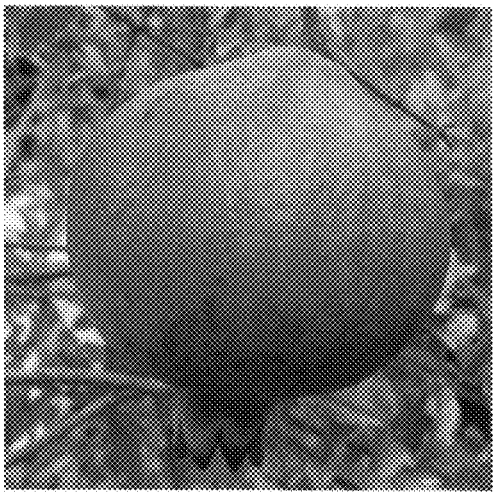

The photograph in FIG. 5 provides a close of view of a mature fruit of 'PQ2009'.

The colors in the photographs are as close as possible with digital photography techniques available, the color values cited in the detailed botanical description accurately describe the colors of the new pomegranate.

DETAILED BOTANICAL DESCRIPTION

The following is a detailed description of two year-old plants of 'PQ2009' as grown in 15-gallon containers in Alpharetta, Ga. The phenotype may vary somewhat with variations in temperature, day length, light intensity, soil types and water and fertility levels, without, however, any variance in the genotype. The color determination is in accordance with The 2007 R.H.S. Colour Chart of The Royal Horticultural Society, London, England, except where general color terms of ordinary dictionary significance are used.

General description:

*Blooming period.*—Blooms from May until first frost in Georgia.

*Plant type.*—Deciduous fruit producing tree.

*Plant habit.*—Plants are naturally multi-stemmed and upright to arching, can be pruned into a single stem but suckers will continuously emerge.

*Plant size.*—Reaches an average of 1.5 m in height and 1.2 m in width as grown in 15-gallon containers for two years in Georgia.

*Growth rate.*—Very vigorous in first two years, then more moderate.

*Diseases resistance.*—Disease susceptibility and resistance in comparable with other *Punica* cultivars and no pest problems have been observed under nursery conditions.

*Cold hardiness.*—At least in U.S.D.A. Zone 8, first year plants in 3 gallon containers exposed to temperatures below −12° C. (10° F.) exhibited significant damage with 50% loss observed.

*Roots.*—Fibrous and fine, well-branched.

*Propagation.*—Hardwood cuttings from suckers and branches.

Description of stems:

*Trunk description.*—Multi-stemmed from base, an average of 6 main branches from base of un-pruned plants, an average of 3.2 cm in diameter observed 3 to 25 cm (consistent until first branch) above soil level.

*Branching habit.*—Moderately branched with branches held at an average angle of 30° from main stem and secondary branches held at an average angle of 45° to the main stem.

*Branch strength.*—Strong and flexible, branches will arch in flower and with fruit set, however the branches do not split or break.

*Branch surface.*—New growth; glabrous and slightly satiny, maturing wood (dormant); finely barked, mature bark; finely barked with stringy exfoliation.

*Internode length.*—An average of 2.5 cm, leaf internode length on secondary stems; an average of 2 cm.

*Branch color.*—Emerging 181C, matures to a blend of 138A and 197A, trunk primarily 197A.

*Branch size.*—Variable in length, however an average of 1 m and an average of 6 mm in width at the base and 2 mm in width near apex, secondary branches an average of 18 cm in length and 2 mm in width.

*Stipules.*—None observed.

*Lenticels.*—Not conspicuous.

Leaf description:

*Leaf division.*—Simple.

*Leaf shape.*—Lanceolate-oblong.

*Leaf arrangement.*—Opposite and occasionally whorled or alternate.

*Leaf size.*—Mature to an average of 7 cm in length and 1.7 cm in width.

*Leaf apex.*—Acute.

*Leaf base.*—Cuneate.

*Leaf surface.*—Glabrous and satiny on both surfaces.

*Leaf substance.*—Moderately thick.

*Leaf margin.*—Entire, very slightly undulate.

*Leaf color.*—Upper and lower surface emerging leaves; 144A, heavily suffused with 187A, young leaves upper and lower surface; 144A, slightly suffused with 175A, mature leaves upper surface 137A, mature leaves lower surface 138A.

*Leaf venation.*—Pinnate, color matches leaf color on both surfaces with mid rib on both surfaces slightly suffused with 178A.

*Petiole.*—Slightly winged, average of 5 mm in length and 1 mm in diameter, 148A in color with wings suffused with 175A, glabrous surface.

*Thorns.*—Occasionally present at leaf axils, up to 1 cm in length and 1.5 mm in diameter, 178A in color.

Flower description:

*Flowering period.*—From early spring until a hard frost, without an obvious rest period; timing is temperature dependent.

*Inflorescence type.*—Single to 3-flowered at terminus of branches and occasionally single at lower nodes, petals are fleeting with sepal portion persistent at apex of fruit.

*Flower type.*—Funnelform.

*Number of flowers.*—1 to 7 per lateral branch (most typically 3).

*Flower buds.*—Oblong-obovate in shape, up to 3.5 cm in length and 1.7 cm in diameter, a blend of N25A, N30A and N30B in color, satiny and waxy surface.

*Flower size.*—Average of 4.5 cm in diameter, an average of 3.5 cm in depth.

*Flower fragrance.*—None.

*Flower aspect.*—Upright to horizontal to stem.

*Petals.*—Consistently 6, base is fused to inner surface of sepals, obovate-rounded in shape, rounded apex, broadly cuneate base, undulate margin, average of 2 cm in length and width, color of upper and lower surface; a blend of N25A, N30A and N30B, surface is crinkled and glabrous, thin substance, fleeting.

*Sepals*.—6, fused calyx with apex free, fused calyx when flower is open an average of 3 cm in length and 1.5 cm in width, with free portions; held horizontal, triangular in shape, average of 7 mm in length and 6 mm in width (at base) and narrowly acute apex, color of outer and inner surface; a blend of N25A, N30A, and N30B, persistent through fruit development.

*Peduncle*.—175A in color, an average of 2 mm in length and width, glabrous waxy surface.

*Pistil*.—1, style is 145D in color and suffused with N30B, triangular base (3 mm in length) with narrow tube (3 mm in length), stigma is 145C in color, globose in shape, and <1 mm in diameter, ovaries inferior, comprised of numerous locules and 23D in color.

*Stamens*.—About 80, filaments are fused into inner surface of calyx, N30B in color, and an average of 4 mm in length, anthers are disk shaped, dorsifixed, curled under and 23D in color, pollen is moderate in quantity and 162B in color.

Fruit description:

*Pollination mechanism*.—Self-compatible, but cross-pollination is preferred and increases fruit set.

*Fruit harvest*.—First picking is generally in October, last picking is generally in December, containers overwintered in a heated greenhouse ripen fruit as early as August.

*Fruit type*.—Berry.

*Fruit size*.—Average of 8.5 cm in diameter, 9.5 cm in height.

*Fruit shape*.—Globose in shape with persistent calyx at apical end.

*Fruit symmetry*.—Roughly symmetrical both horizontally or vertically.

*Fruit stem*.—Average of 3.5 mm in length and width, stringy barked surface, color 197A.

*Fruit flesh*.—Comprised of numerous v-shaped locules (average of 6) in the center containing an average of 240 seeds contained in juicy seedcoats (sarcotesta) per berry, locules are surrounded by a spongy membrane 11B in color.

*Fruit skin*.—Color immature; 18B with some shading of N30A and some small spots of 199*a*, color mature; 20B and heavily suffused with 46A and 46B and some irregular markings of 199A, surface is lustrous, leathery, and slightly pitted.

*Seeds* (*arils*).—Numerous, an average of 7 mm in length and 3 mm in width, irregular in shape but roughly oblong/kidney-shaped, 161C in color, juicy seed coat; an average of 1 cm in diameter, variable in shape, primarily N34A in color with translucent areas, glossy surface.

*Fruit flavor*.—Sweet and slightly tangy, low astringency.

*Fruit weight*.—Average of 250 grams (up to 451 grams).

*Fruit aroma*.—None detected.

*Fruit keeping quality*.—About 4 weeks at room temperatures before rind begins to mummify and fruit volume begins to shrink from dehydration, 6 to 8 weeks if refrigerated with humidity control.

*Fruit use*.—Used for fresh consumption by home gardeners.

It is claimed:

1. A new and distinct variety of *Punica granatum* plant named 'PQ2009' as described and illustrated herein.

* * * * *